United States Patent
Layman et al.

(10) Patent No.: US 9,498,360 B2
(45) Date of Patent: Nov. 22, 2016

(54) STENT AND METHOD OF USE

(71) Applicants: STRYKER CORPORATION, Kalamazoo, MI (US); STRYKER NV OPERATIONS LIMITED, Dublin (IE)

(72) Inventors: Ted W. Layman, Park City, UT (US); Stephen C. Porter, Piedmont, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 205 days.

(21) Appl. No.: 14/204,173

(22) Filed: Mar. 11, 2014

(65) Prior Publication Data

US 2014/0277391 A1    Sep. 18, 2014

Related U.S. Application Data

(60) Provisional application No. 61/792,252, filed on Mar. 15, 2013.

(51) Int. Cl.
*A61F 2/915* (2013.01)
*A61F 2/89* (2013.01)
*A61F 2/962* (2013.01)

(52) U.S. Cl.
CPC ............ *A61F 2/915* (2013.01); *A61F 2/89* (2013.01); *A61F 2/962* (2013.01); *A61F 2002/9155* (2013.01); *A61F 2002/91558* (2013.01); *A61F 2002/91566* (2013.01); *A61F 2002/91575* (2013.01)

(58) Field of Classification Search
CPC ............ A61F 2/94; A61F 2/86; A61F 2/915; A61F 2002/9155; A61F 2002/91583; A61F 2002/91575; A61F 2/89
See application file for complete search history.

(56) References Cited

U.S. PATENT DOCUMENTS

| | | | | |
|---|---|---|---|---|
| 6,053,940 A * | 4/2000 | Wijay | ...... | A61F 2/90 606/108 |
| 6,171,334 B1 * | 1/2001 | Cox | ...... | A61F 2/91 623/1.15 |
| 6,200,337 B1 * | 3/2001 | Moriuchi | ...... | A61F 2/91 606/198 |
| 6,620,201 B1 * | 9/2003 | Nadal | ...... | A61F 2/91 623/1.15 |
| 6,997,944 B2 * | 2/2006 | Harrison | ...... | A61F 2/91 623/1.15 |
| 7,789,904 B2 * | 9/2010 | Von Oepen | ...... | A61F 2/91 606/198 |
| 8,287,587 B2 * | 10/2012 | Moriuchi | ...... | A61F 2/91 623/1.15 |
| 2003/0225449 A1 * | 12/2003 | Denison | ...... | A61F 2/91 623/1.15 |
| 2004/0015226 A1 * | 1/2004 | Pelton | ...... | A61F 2/91 623/1.16 |
| 2005/0187606 A1 * | 8/2005 | Gregorich | ...... | A61F 2/91 623/1.15 |
| 2006/0253187 A1 * | 11/2006 | Moriuchi | ...... | A61F 2/91 623/1.15 |
| 2007/0038289 A1 * | 2/2007 | Nishide | ...... | A61F 2/91 623/1.16 |
| 2008/0051876 A1 * | 2/2008 | Ta | ...... | A61F 2/91 623/1.16 |

(Continued)

Primary Examiner — Christian Sevilla
Assistant Examiner — Seema Mathew
(74) Attorney, Agent, or Firm — Vista IP Law Group, LLP

(57) ABSTRACT

A stent configured for implantation in a body lumen includes a plurality of radially expandable circumferential segments, and an axially expandable connecting member connecting adjacent circumferential segments of the plurality. The stent has a relaxed, axially contracted configuration in which the connecting member is contracted axially and each circumferential segment is nested with at least one adjacent circumferential segment. The stent also has a delivery, axially expanded configuration in which the connecting member is expanded axially, and an axial distance between adjacent circumferential segments of the plurality is greater than when the stent is in its relaxed configuration.

15 Claims, 4 Drawing Sheets

(56) References Cited

U.S. PATENT DOCUMENTS

| | | | | |
|---|---|---|---|---|
| 2008/0051877 A1* | 2/2008 | Hsiao | ................ | A61F 2/91 623/1.16 |
| 2008/0086190 A1* | 4/2008 | Ta | ................ | A61F 2/915 623/1.11 |
| 2013/0123905 A1* | 5/2013 | Abunassar | ................ | A61F 2/915 623/1.16 |

\* cited by examiner

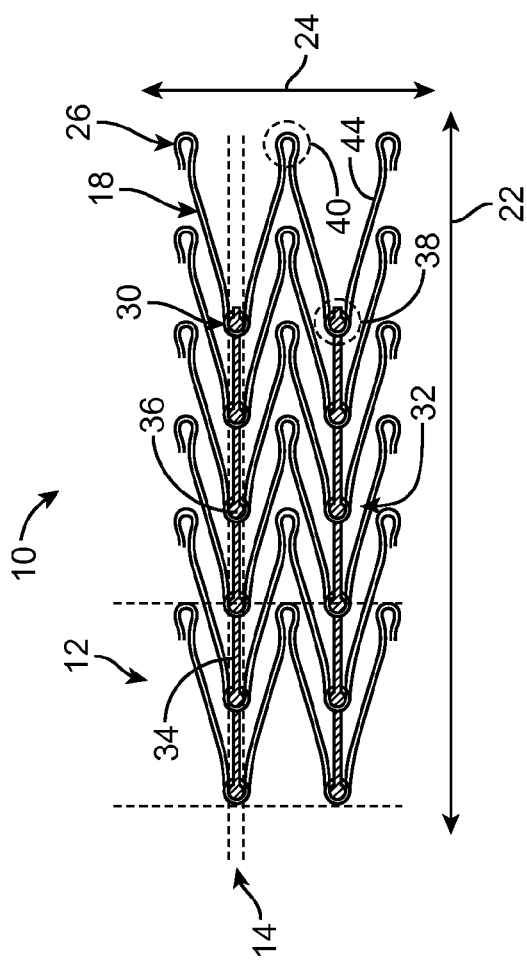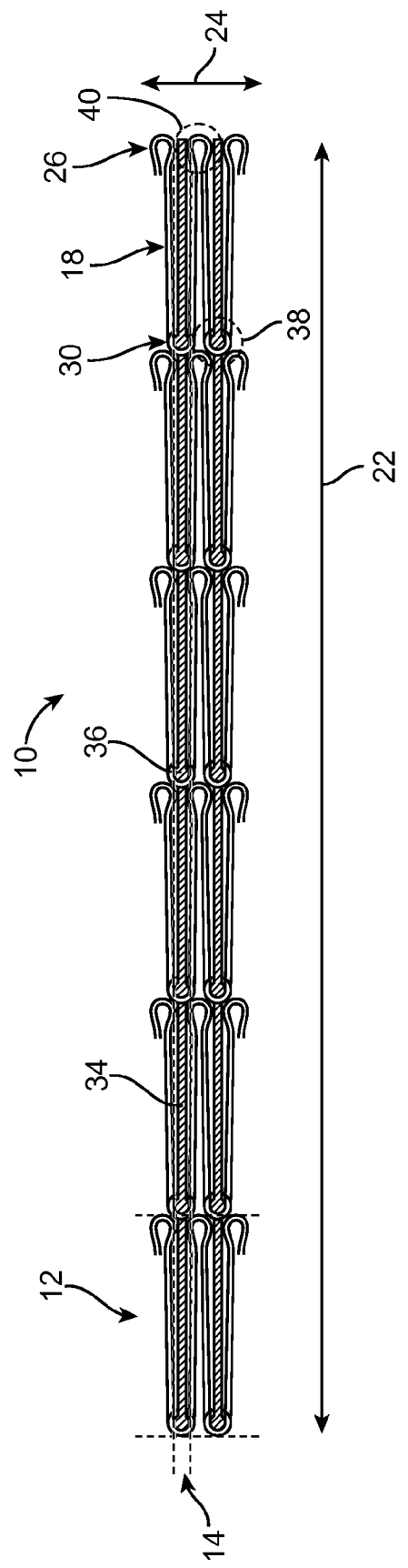

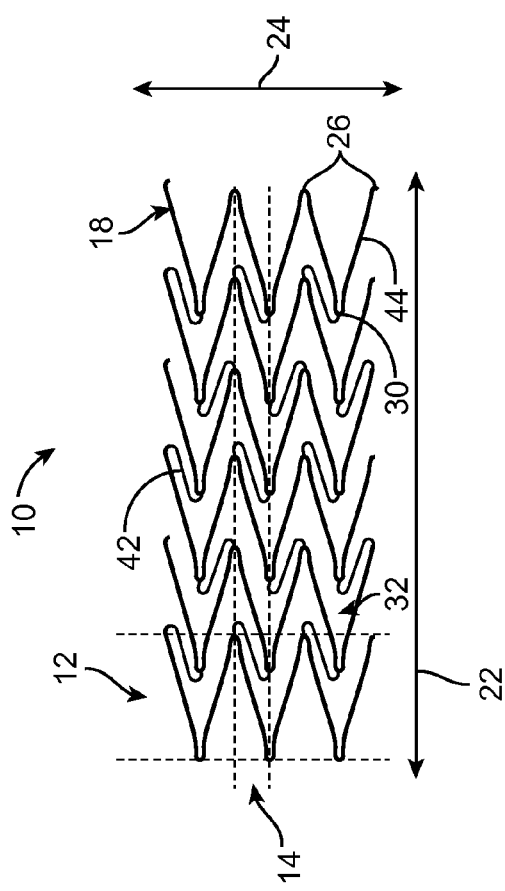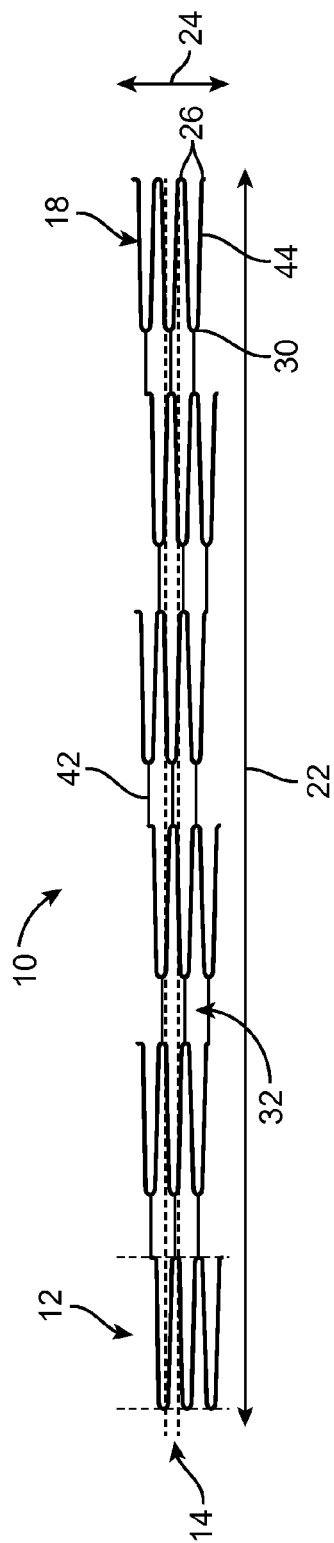
FIG. 3A
FIG. 3B

STENT AND METHOD OF USE

RELATED APPLICATION DATA

The present application claims the benefit under 35 U.S.C. §119 to U.S. Provisional Application Ser. No. 61/792,252, filed Mar. 15, 2013. The foregoing application is hereby incorporated by reference into the present application in its entirety.

FIELD

The present disclosure relates generally to medical devices and intravascular medical procedures and, more particularly, to stents and methods of using same.

BACKGROUND

The use of intravascular medical devices has become an effective method for treating many types of vascular disease. In general, a suitable intravascular device is inserted into the vascular system of the patient and navigated through the vasculature to a desired target site. Using this method, virtually any target site in the patient's vascular system may be accessed, including the coronary, cerebral, and peripheral vasculature.

Medical devices such as stents, stent grafts, and vena cava filters, collectively referred to hereinafter as stents, are often utilized in combination with a delivery device for placement at a desired location within the body. A medical prosthesis, such as a stent for example, may be loaded onto a stent delivery device and then introduced into the lumen of a body vessel in a configuration having a reduced diameter. Once delivered to a target location within the body, the stent may then be expanded to an enlarged configuration within the vessel to support and reinforce the vessel wall while maintaining the vessel in an open, unobstructed condition.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent may be biased so as to expand upon release from the delivery catheter and/or include a shape-memory component which allows the stent to expand upon exposure to a predetermined condition. Some stents may be characterized as hybrid stents which have some characteristics of both self-expandable and balloon expandable stents.

Stents may be constructed from a variety of materials such as stainless steel, Elgiloy, nickel, titanium, nitinol, shape memory polymers, etc. Stents may also be formed in a variety of manners as well. For example a stent may be formed by etching or cutting the stent pattern from a tube or sheet of stent material; a sheet of stent material may be cut or etched according to a desired stent pattern whereupon the sheet may be rolled or otherwise formed into the desired substantially tubular, bifurcated or other shape of the stent; one or more wires or ribbons of stent material may be woven, braided or otherwise formed into a desired shape and pattern. The density of the braid in braided stents is measured in picks per inch. Stents may include components that are welded, bonded or otherwise engaged to one another.

Flow diverting stents may treat a brain aneurysm by disrupting the flow of blood into the aneurysm using a mesh of biocompatible material placed over the aneurysm neck. Subsequently, the blood in the aneurysm stagnates and, in time, forms a thrombosis to close the aneurysm. Flow diverting stents may treat a brain aneurysm by providing resistance to blood inflow to the aneurysm. The mesh of a flow diverting stent must have sufficient pore density to disrupt the inflow to the aneurysm, but enough open area to allow side branches and perforating arteries to remain patent. To increase the therapeutic effectiveness of a flow diverting stent, the middle segment of the stent, which impedes blood flow into the aneurysm, has a low porosity.

Adjunctive neurovascular stents may treat wide necked aneurysms by providing a scaffold for retaining coils in such wide necked aneurysms. Some examples of these are the Neuroform™, Enterprise™, and the Leo™ stents. Adjunctive stents typically can be made with higher porosity (lower pore density and larger pore sizes) than flow diverting stents.

Porosity of stent material is a measure of the tendency of that material to allow passage of a fluid. A stent material's porosity index (PI) is defined as one minus the ratio of stent metal surface area to artery surface area covered by the stent. Higher porosity means that the stent material has less metal surface area compared to artery surface area and lower porosity means that the stent has more metal surface area compared to artery surface area.

Typically, a stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the stent is caused or allowed to expand to a predetermined diameter in the vessel. Many delivery devices include sheaths or catheters, and delivery members having bumpers thereon to push and pull stents through the sheaths and catheters. A catheter may be bent while navigating through torturous vasculature.

Some stents are deployed by loading them proximally from an introducer sheath into a pre-positioned microcatheter. The stent is then pushed through the microcatheter for approximately 150 cm until it is deployed from the distal end of the catheter at the treatment site. This "empty catheter" technique is different from the more traditional self-expanding stent delivery technique, which includes pre-loading the stent adjacent the distal end of the catheter and then simultaneously tracking the stent and catheter to the treatment site. The evolution of the empty catheter technique was driven by the extremely tortuous anatomy commonly found in the intracranial circulation.

First generation flow diverting stents were braided constructions of nitinol or other alloys. Typically, these have been constructed from small wire filaments around 0.0006 inches to 0.002 inches in diameter, and have between 24 and 96 wires. Braided first generation flow diverting stents work very well in many ways. They conform to tortuous anatomy well, they provide relatively uniform porosity, they are very flexible in their expanded state, and they can be reduced to relatively small profiles inside the delivery catheter.

Perceived problems with current first generation flow diversion stents include variable foreshortening of braided stents upon delivery, which makes deployed length unpredictable. Another perceived problem is increased rigidity when stents are compressed for delivery, which reduces the accuracy of deployment and the trackability of longer stents. Yet another perceived problem is the radial profile of braided stents, which reduces the size of vessel lumens. Still another perceived problem is the "fish-mouth" effect when braided stents do not expand at the distal or proximal ends, which creates difficulty in re-crossing the stent and increases thromboembolic complications at the stent ends. Another perceived problem is sub-optimal anchoring due to low opening force and the nature of braided stents, which prevents the distal end from opening independently of proximal portions. Yet another perceived problem is increasing radial profile with decreasing porosity (i.e., more braided wires), which increases stiffness and makes delivery more difficult. This perceived problem is also found in larger stents, which have more braided wires. Still another perceived problem is the unconstrained ends of braided stents, which may pose a risk to the body lumen into which the stent is deployed. Also, the pressure that delivery exerts on the ends of braided stents may also disrupt the uniformity of the braided ends upon deployment.

SUMMARY

In one embodiment of the disclosed inventions, a stent configured for implantation in a body lumen includes a plurality of radially expandable circumferential segments, and an axially expandable connecting member connecting adjacent circumferential segments of the plurality. The stent has a relaxed, axially contracted configuration in which the connecting member is contracted axially and each circumferential segment is nested with at least one adjacent circumferential segment. The stent also has a delivery, axially expanded configuration in which the connecting member is expanded axially, and an axial distance between adjacent circumferential segments of the plurality is greater than when the stent is in its relaxed configuration.

In some embodiments, when the stent is in its delivery configuration, the connecting member is biased to contract axially, and the circumferential segments are biased to expand radially. The plurality of circumferential segments and the connecting member may be configured such that radial compression of the circumferential segments exerts an axially expanding force on the connecting member. Each circumferential segment may include a plurality of chevron-shaped members aligned in a same direction, where each chevron-shaped member of a respective circumferential segment nests with at least one adjacent chevron-shaped member when the stent is in its relaxed configuration.

In some embodiments, the stent includes a plurality of axially expandable connecting members connecting adjacent circumferential segments of the plurality of circumferential segments, where each connecting member is contracted axially when the stent is in its relaxed configuration, and expanded axially when the stent is in its delivery configuration. A chevron-shaped member of a first circumferential segment may be connected via a respective one of the plurality of connecting members to a chevron-shaped member of a second circumferential segment. Each connecting member may be a sinusoid-shape having an amplitude that is reduced when the connecting member is expanded axially.

Respective circumferential segments and connecting members may be configured such that, when the stent is in its delivery configuration, mechanical interference between adjacent circumferential segments retains the connecting members in an expanded state. Each connecting member may be resilient and elastically expandable to change its length, such that, when the connecting member is expanded axially, it is biased to contract axially.

In some embodiments, each chevron-shaped member of a respective circumferential segment is directly connected to at least one adjacent chevron-shaped member of that circumferential segment. In other embodiments, each chevron-shaped member of a circumferential segment may be connected to an adjacent chevron-shaped member of that segment by a respective connecting member.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1A-3B are detailed top views of stents according to various embodiments of the disclosed inventions that have been cut open along their lengths and unrolled into flat sheets, with select components of the stents omitted for clarity. While FIGS. 1A-3B omit select elements of the stents depicted therein, one of skill in the art will recognize that FIGS. 1A-3B depict patterns that can be repeated in the axial and circumferential directions to form stents of any size.

DETAILED DESCRIPTION OF THE ILLUSTRATED EMBODIMENTS

Figure 1A:
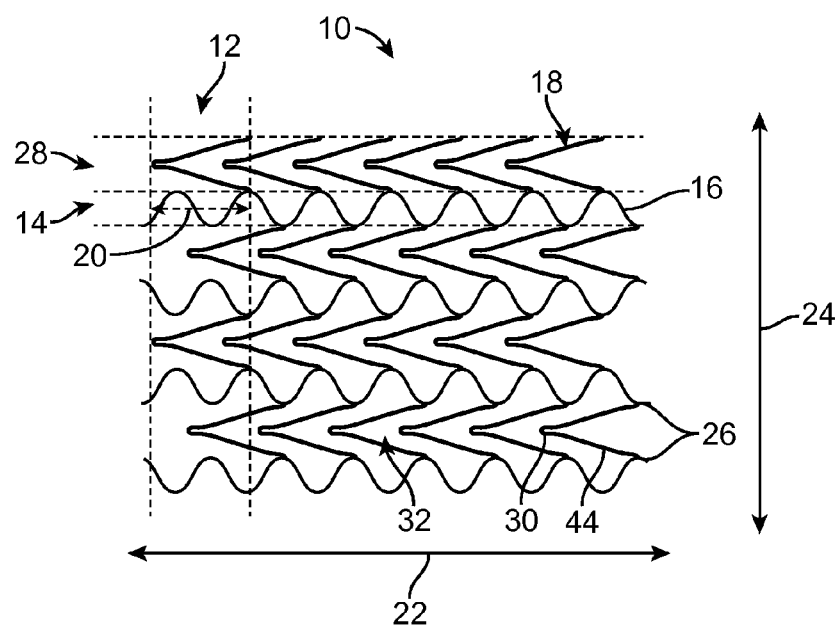

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 1B:
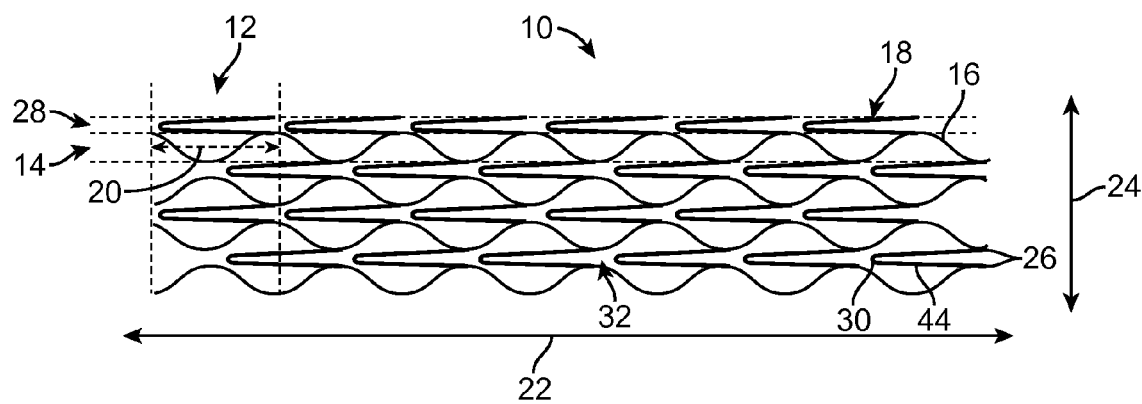

FIGS. 1A and 1B depict a portion of a stent 10 that has been cut open along its length and unrolled into a flat sheet. FIG. 1A depicts the stent 10 in its axially contracted/radially expanded ("relaxed") configuration, which is the open or deployed configuration. FIG. 1B depicts the stent 10 in its axially expanded/radially contracted ("delivery") configuration. The stent 10 has a plurality of radially expandable ("circumferential") segments 12 and a plurality of axially expandable ("connecting") segments 14. Each connecting segment 14 is a sinusoid-shaped member 16, have an "amplitude" and a "wavelength". Each circumferential segment 12 is formed from an alternating series of chevron-shaped members 18 and portions 20 of sinusoid-shaped members 18. Each chevron-shaped member 18 has a vertex 30 and two bases 26. In the relaxed configuration, the circumferential segments 12 are radially expanded and the connecting segments 14 are axially contracted.

The sinusoid-shaped member 16 is generally aligned with the longitudinal axis 22 of the stent 10. While only a portion of the stent 10 is depicted in FIGS. 1A and 1B, the longitudinal axis 22 encompasses the entire axial length of the stent 10. The shape and flexibility of the sinusoid-shaped member 16 allows it to lengthen its "wavelength" under axial tension, thereby elongating the sinusoid-shaped member 16 and the stent 10 in the axial direction, i.e. along the stent's 10 longitudinal axis 22, as shown in FIG. 1B. Within the operating range of the stent 10, the sinusoid-shaped member 16 bends elastically as it lengthens, biasing the sinusoid-shaped member 16 to return to its sinusoid shape when the stent 10 is in its relaxed configuration, as depicted in FIG. 1A.

As described above and depicted in FIG. 1A, each circumferential segment 12 is formed from an alternating series of chevron-shaped members 18 and portions 20 of sinusoid-shaped members 16. Each chevron-shaped member 18 is connected to two sinusoid-shaped members 16, with one sinusoid-shaped member 16 connected at each base 26 of the chevron-shaped member 18. Accordingly, the chevron-shaped members 18 of a stent 10 also form axial rows 28 that are interlaced with sinusoid-shaped members 16.

The chevron-shaped members 18 of any axial row 28 are aligned along the longitudinal axis 22 of the stent 10, with the vertices 30 of the chevron-shaped members 18 pointed in the same axial direction. Although all the chevron-shaped members 18 in the various axial rows 18 depicted in FIG. 1A are pointed in the same axial direction, in other embodiments (not depicted), the chevron-shaped members 18 in different axial rows 28 may be pointed in opposite directions.

When the stent 10 is in the relaxed configuration, as shown in FIG. 1A, the "wavelength" of the sinusoid-shaped members 14 is reduced (compared to the delivery configuration depicted in FIG. 1B). The reduced "wavelength" causes the chevron-shaped members 18 in each axial row 18 to "nest" with each other. Chevron-shaped members 18 are nested when the peak of one chevron-shaped member 18 enters the circumscribed space of an adjacent chevron-shaped member 18. When nested, the vertex 30 of a chevron-shaped member 18 in one circumferential segment 12 is disposed between the base 26 and vertex 30 of a chevron-shaped member 18 in an adjacent circumferential segment 12. This nesting reduces the size of the opening 32 defined by axially adjacent chevron-shaped members 18 and circumferentially adjacent sinusoid-shaped members 16, thereby reducing the porosity of the stent 10 compared to more traditional stents, which have minimal axial contraction when circumferentially expanded. Nesting also increases the stiffness of the stent 10, allowing it to better engage a body lumen into which it is deployed, when compared to more traditional stents.

When the stent 10 is in the delivery configuration, as shown in FIG. 1B, the "wavelength" of the sinusoid-shaped members 14 is increased (compared to the relaxed configuration depicted in FIG. 1A). The increased "wavelength" causes the chevron-shaped members 18 in each axial row 18 to axially separate, i.e. un-nest, from each other. This axial separation increases the size of the opening 32 defined by axially adjacent chevron-shaped members 18 and circumferentially adjacent sinusoid-shaped members 16, thereby increasing the porosity of the stent 10. However, circumferential compression of the circumferential segments 12 decreases the porosity of the stent 10. Depending on the relative dimensions and flexibilities of the various parts of the stent 10, the net porosity change from the expanded to the delivery configuration may be an increase in, a decrease in, or no change to porosity of the stent 10.

Similarly, axial separation of the chevron-shaped members 18 decreases the stiffness of the stent 10, but circumferential compression of the circumferential segments 12 increases the stiffness of the stent 10. Depending on the relative dimensions and flexibilities of the various parts of the stent 10, the net change in stiffness from the expanded to the delivery configuration may be an increase in, a decrease in, or no change to stiffness of the stent 10.

When a stent 10 is radially compressed for delivery through a catheter, the bases 26 of each chevron-shaped member 18 are brought closer to each other and the "amplitude" of the sinusoid-shaped member 16 is reduced, thereby decreasing the circumferential dimension 24 of the circumferential segments 12 of the stent 10. While only a portion of the stent 10 is depicted in FIGS. 1A and 1B, the circumferential dimension 24 encompasses the entire circumference of the stent 10. Due to the geometry of the sinusoid-shaped member 16, decreasing its "amplitude" by compressing the "waves" also increases the "wavelength" of the sinusoid-shaped member 16. Accordingly, radially compressing the stent 10 increases the length of the sinusoid-shaped member 16 and the stent 10.

When a chevron-shaped member 18 is bent to bring its bases 26 closer to each other, the chevron-shaped member 18 bends elastically to biased the chevron-shaped member 18 to return to its "open" shape when the stent 10 is in its relaxed configuration, as depicted in FIG. 1A. Therefore, when the stent 10 is compressed into its delivery configuration (FIG. 1B), the stent 10 is biased to radially expand and axially contract by the elastically bent and "closed" chevron-shaped members 18 and the elastically bent and lengthened sinusoid-shaped members 16 (described above), respectively. Radially compressing and restraining the stent 10 (e.g., with a delivery catheter) prevents the elongated sinusoid-shaped members 16 from contracting because they cannot increase their "amplitudes" to increase their "wavelengths."

When the stent 10 is released from the catheter for delivery and implantation, the chevron-shaped members 18 resiliently "open" to expand the stent 10 radially. At the same time, the sinusoid-shaped members 16 resiliently increase their "amplitude," further expanding the stent 10 radially. Expanding the stent 10 radially exerts a radially outward force, which facilitates anchoring of the stent 10 in the body lumen into which it is delivered. Simultaneously, the sinusoid-shaped members 16 resiliently decrease their "wavelength," thereby contracting along the longitudinal axis 22 of the stent 10 and contracting the stent 10 axially. Contracting the stent 10 axially reduces the porosity of the stent 10, facilitating the function of flow diverting stents 10. For adjunctive stents 10, which do not require such low porosity, the reduction in porosity with axial contraction upon deployment enables adjunctive stents 10 to achieve the required porosity either with less material or with the same amount of material, but a more compressed delivery diameter, when compared to more traditional adjunctive stents.

When the stent 10 is placed under axial tension, the sinusoid-shaped members 16 are stretched axially. As the sinusoid-shaped member 16 lengthens, the "amplitude" of the sinusoid-shaped member 16 decreases, thereby decreasing the circumferential dimension 24 of the circumferential segments 12 of the stent 10, as depicted in FIG. 1B. However, axially stretching the stent 10 does not "close" the chevron-shaped members 18. While axial tension will partially compress the stent 10 in the radial direction, radial force must be applied to fully compress the stent 10 in the radial direction.

The stent 10 is formed in a single layer between the proximal end and the distal end. In at least one embodiment, the stent 10 is etched or cut (e.g., by laser) from a solid tube comprised of metals, polymers, composites and other materials, such as PET, PTFE, stainless steel, Elgiloy, nickel, titanium, Nitinol, shape memory polymers, and other biocompatible materials. The stent 10 may also be cut from a flat sheet and welded at a seam (e.g., spot-welded). The stent 10 may also be vapor deposited (e.g., Nitinol) on a mandrel that is machined with the desired pattern. The stent 10 can have a molded or other non-wire construction. Moreover, various parts of the stent 10 (e.g., sinusoid-shaped member 16 and the chevron-shaped members 18) can be made as separate parts, then joined together (e.g., by welding or adhesives).

FIGS. 2A and 2B depict a portion of another stent 10 that has been cut open along its length and unrolled into a flat sheet. FIGS. 2A and 2B depict the stent 10 in relaxed and delivery configurations, respectively. Like the stent 10 depicted in FIGS. 1A and 1B, the stent 10 depicted in FIGS. 2A and 2B has a plurality of circumferential segments 12 and a plurality of connecting segments 14. Each circumferential segment 12 is formed from a series of chevron-shaped members 18 connected to each other at their bases 26. Each connecting segment 14 is a linear member 34 having enlargements 36 disposed thereon at regular intervals.

The vertices 30 of the chevron-shaped members 18 each have a ring 38 formed thereon. The enlargements 36 of the linear members 34 are attached to the rings 38 of the chevron-shaped members 18, thereby connecting the linear members 34 to the chevron-shaped members 18. The process of bonding the linear members 34 to the rings 38 (e.g., with an adhesive) may form the enlargements 36 at the points of attachment. The bases 26 of the chevron-shaped members 18 each have an eyelet 40 formed thereon at the location where circumferentially adjacent chevron-shaped members 18 are attached to each other.

The linear members 34 are elastically expandable in an axial direction, such that, when they are placed under axial tension, they increase their length and become biased to contract axially by decreasing their length. Accordingly, when the stent 10 is in the delivery configuration, as shown in FIG. 2B, the linear members 34 are elastically expanded and biased to return the stent 10 to the relaxed configuration, as shown in FIG. 2A.

Independent of the linear members 34, the chevron-shaped members 18 are biased to "open" by separating their bases 26, similar to the chevron-shaped members 18 in the stent 10 depicted in FIGS. 1A and 1B. Accordingly, when the stent 10 is radially compressed, as shown in FIG. 2B, the chevron-shaped members 18 are elastically "closed," by bringing their bases 26 together, and biased to return the stent 10 to the radially expanded configuration, as shown in FIG. 2A.

The stent 10 depicted in FIGS. 2A and 2B is both radially compressed and axially expanded, as shown in FIG. 2B, before it is loaded into a catheter for delivery. When the stent 10 is radially compressed, the eyelets 40 of each chevron-shaped member 18 are brought closer to each other, with the legs 44 of the chevron-shaped members 18 almost parallel to each other. The vertices 30 of axially adjacent chevron-shaped members 18 are removed from each other when the stent 10 is axially expanded until adjacent circumferential segments 12 no longer nest or overlap. This is accomplished when the vertices 30 are pulled past the eyelets 40 of the axially adjacent chevron-shaped members 18. After the vertices 30 are pulled past the eyelets 40 of the axially adjacent chevron-shaped members 18 and the eyelets 40 are compressed together, the eyelets 40 of a first chevron-shaped member 18 prevent axial travel of the vertex 30 of an axially adjacent second chevron-shaped member 18 past the eyelets 40 of the first chevron-shaped member 18. The juxtaposition of the vertices 30 and eyelets 40 of axially adjacent chevron-shaped members 18 maintains axial tension on the linear members 34 until the stent is released from the catheter. When the linear members 34 are elongated, the chevron-shaped members 18 do not overlap each other in an axial direction.

When the stent 10 depicted in FIGS. 2A and 2B is released from the catheter, the compressed chevron-shaped members 18 expand radially. Radial expansion moves the eyelets 40 of each chevron-shaped member 18 away from each other, and allows the linear members 34 to contract, thereby causing adjacent circumferential segments 12 to nest with each other.

The circumferential segments 12 depicted in FIGS. 2A and 2B may be formed as separate rings from lengths of bent wire. The circumferential segments 12 also may be made from a single wire bent to form a helical series of chevron-shaped members 18. In either case, connecting segments 14 are attached to the rings 38 formed at the vertex 30 of each chevron-shaped member 18 to connect (or further connect) the circumferential segments 12. The connected members 14 may be formed of an elastic polymer and bonded to the rings 38 with an adhesive. As described above, the adhesive may form the enlargements 36 on the connecting segments 14. The stent 10 is assembled with the circumferential segments 12 and connecting segments 14 in their relaxed states (i.e., radially expanded circumferential segments 12 and axially contracted connecting segments 14). In these states, the circumferential segments 12 can nest with each other, allowing the connecting segments 14 to connect adjacent circumferential segments 12 when they are closest to each other.

FIGS. 3A and 3B depict a portion of another stent 10 that has been cut open along its length and unrolled into a flat sheet. FIGS. 3A and 3B depict the stent 10 in relaxed and delivery configurations, respectively. Like the stents 10 depicted in FIGS. 1A, 1B, 2A and 2B, the stent 10 depicted in FIGS. 3A and 3B has a plurality of circumferential segments 12 and a plurality of connecting segments 14. Like the stents 10 depicted in FIGS. 2A and 2B, each circumferential segment 12 is formed from a series of chevron-shaped members 18 connected to each other at their bases 26. Each connecting segment 14 is formed from a series of axial connectors 42, where each axial connector 42 connects the vertex 30 of one chevron-shaped member 18 to the base 26 of an axially adjacent chevron-shaped member 18.

In the embodiment depicted in FIGS. 3A and 3B, the axial connectors 42 have a shape memory and change shape as the stent 10 changes configuration. In the relaxed configuration in FIG. 3A, the axial connectors 42 form an "S" shape, and in the delivery configuration in FIG. 3B, the axial connectors 42 are strained into a linear shape. In the delivery configuration, because the vertex 30 of one chevron-shaped member 18 is connected to the base 26 of an axially adjacent chevron-shaped member 18, adjacent circumferential segments 12 (i.e. circumferentially disposed series of chevron-shaped members 18) are circumferentially shifted relative to one another when the stent 10 is stretched from the relaxed configuration (FIG. 3A) to the delivery configuration (FIG. 3B). As shown in FIG. 3B, adjacent circumferential segments 12 are circumferentially shifted so that vertices 30 of one circumferential segment 12 are juxtaposed with bases 26 of an adjacent circumferential segment 12. Optionally, alternating circumferential segments 12 may shift in opposite circumferential directions, with the net effect being that the stent 10 is axially expanded without any change in the circumferential direction and zero net torque.

The shape memory axial connectors 42 are biased into an "S" shape, as shown in FIG. 3A. The axial connectors 42 attached to the vertices 30 of axially adjacent chevron-shaped members 18 are biased to form "S" shapes that bend in opposite directions. Accordingly, no radially expandable segment 12 shifts more than half the width of a chevron-shaped member 18 relative to any other radially expandable segment 12 when the stent 10 is stretched from the relaxed configuration (FIG. 3A) to the delivery configuration (FIG. 3B). The axial connectors 42 may be made from shape memory materials (e.g., Nitinol) and heat-set to impart shape memory biasing the axial connectors 42 into "S" shapes.

Accordingly, the connecting segments 14 are elastically expandable in an axial direction, such that, when they are placed under axial tension, they increase their length, by straightening the "S" shaped axial connectors 42 under tension, as shown in FIG. 3B. Further, straightening the axial connectors 42 biases then to return to their "S" shaped configuration, thereby decreasing the length of the connecting segments 14. Accordingly, when the stent 10 is in the delivery configuration, as shown in FIG. 3B, the axial connectors 42 are biased to return the stent 10 to the relaxed configuration, as shown in FIG. 3A.

Independent of the axial connectors 42, the chevron-shaped members 18 are biased to "open" by separating their bases 26, similar to the chevron-shaped members 18 in the stent 10 depicted in FIGS. 1A, 1B, 2A and 2B. Accordingly, when the stent 10 is radially compressed, as shown in FIG. 3B, the chevron-shaped members 18 are elastically "closed," by bringing their bases 26 together, and biased to return the stent 10 to the radially expanded configuration, as shown in FIG. 3A.

The stent 10 depicted in FIGS. 3A and 3B is both radially compressed and axially expanded, as shown in FIG. 3B, before it is loaded into a catheter for delivery. The "closed" chevron-shaped members 18 of axially adjacent circumferential segments 12 prevent the axial connectors 42 from returning to the "S" shaped configuration, because adjacent circumferential segments 12 cannot nest with "closed" chevron-shaped members 18. Restraining the axial connectors 42, in turn, maintains tension (partially axial) on the axial connectors 42 until the stent 10 is released from the catheter. In the delivery configuration, the axial connectors 42 are in their linear shape and the chevron-shaped members 18 do not overlap each other in an axial direction.

When the stent 10 depicted in FIGS. 3A and 3B is released from the catheter, the compressed chevron-shaped members 18 expand radially. Radial expansion of the chevron-shaped members 18 allows the circumferential segments 12 to nest, thereby allowing the axial connectors 42 to return to the "S" shape. Return of the axial connectors 42 to the "S" shaped configuration circumferentially shifts adjacent circumferential segments 12 relative to each other and juxtaposes vertices 30 of adjacent circumferential segments 12 with each other. This configuration change facilitates nesting of adjacent circumferential segments 12.

The stent 10 depicted in FIGS. 3A and 3B is formed similar to the stent 10 depicted in FIGS. 1A and 1B. The stent 10 may be etched or cut (e.g., by laser) from a solid tube, cut from a flat sheet and welded at a seam (e.g., spot-welded), vapor deposited (e.g., Nitinol) on a mandrel that is machined with the desired pattern, or molded. Moreover, various parts of the stent 10 (e.g., chevron-shaped members 18 and axial connectors 42) can be made as separate parts, then joined together (e.g., by welding or adhesives). The axial connectors 42 are made of heat memory material (e.g., Nitinol or shape memory polymer) and heat-set to impart a shape memory biasing the axial connectors 42 into "S" shapes.

Figure 4:
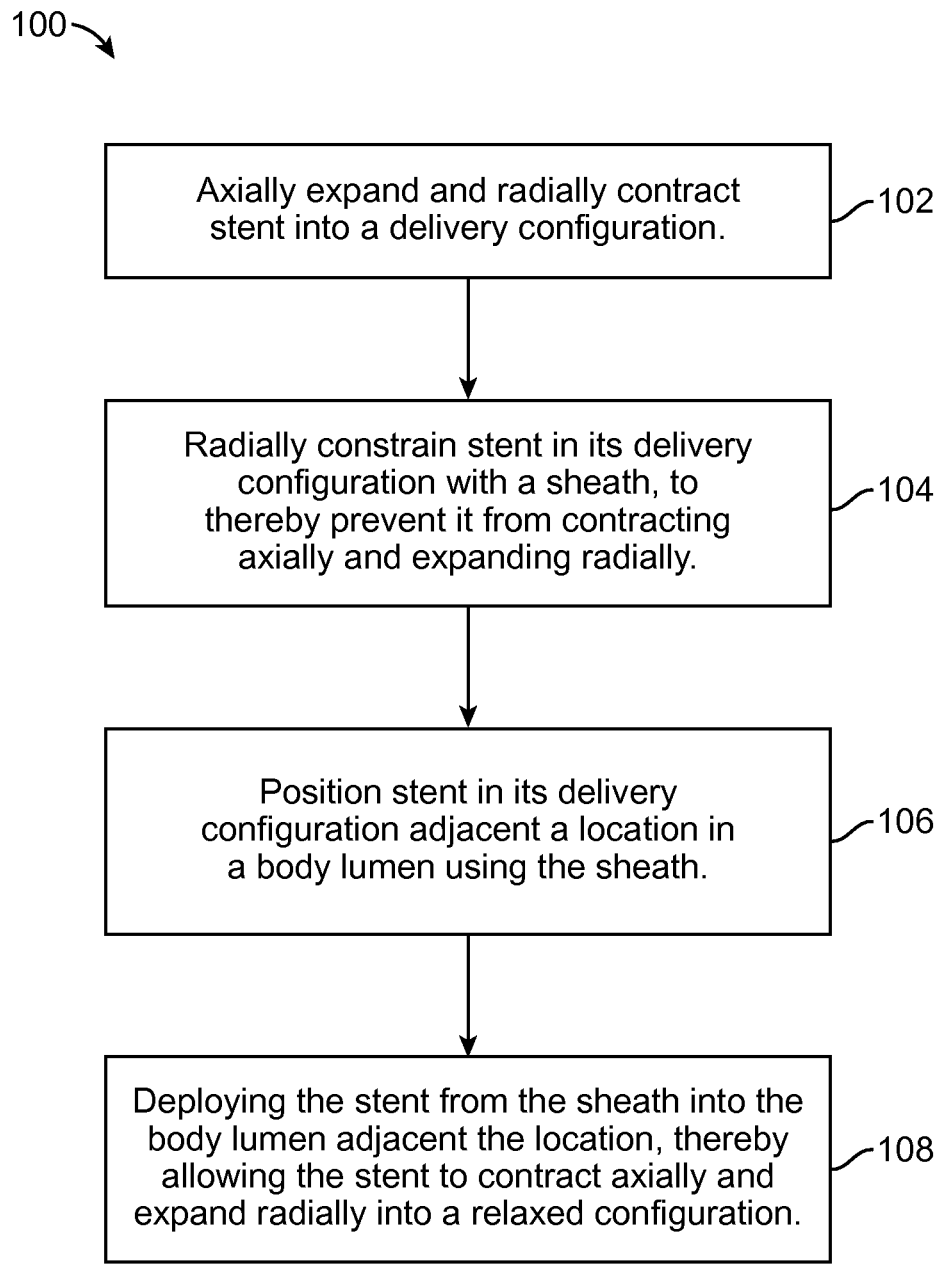
FIG. 4 is a flowchart illustrating a method of using the a stent according to an embodiment of the disclosed inventions.

As depicted in FIG. 4, a method 100 of deploying a stent 10 formed in accordance with these inventions is different from deploying conventional stents, because the stent 10 is first axially expanded and radially contracted into a delivery configuration in step 102. Next, the stent 10 is radially constrained in its delivery configuration with a sheath, to thereby prevent it from contracting axially and expanding radially in step 104. Then, the stent 10 is positioned in its delivery configuration adjacent a location in a body lumen using the sheath in step 106. Finally, the positioned stent is deployed from the sheath into the body lumen adjacent the location, thereby allowing the stent to contract axially and expand radially into a relaxed configuration in step 108.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A stent configured for implantation in a body lumen, comprising:
   a plurality of radially expandable circumferential segments; and
   an axially expandable connecting member connecting adjacent circumferential segments of the plurality,
   wherein the stent has
      an axially contracted configuration in which the connecting member is contracted axially, and a vertex of each circumferential segment is nested between a base and a respective vertex of at least one adjacent circumferential segment, and
      an axially expanded configuration in which the connecting member is expanded axially, the vertex of each circumferential segment is un-nested from the respective at least one adjacent circumferential segment, and an axial distance between adjacent circumferential segments of the plurality is greater than when the stent is in its axially contracted configuration wherein, the connecting member connects a base of a first circumferential segment with a base of an adjacent circumferential segment.

2. The stent of claim 1, wherein, when the stent is in its axially expanded configuration, the connecting member is biased to contract axially, and the circumferential segments are biased to expand radially.

3. The stent of claim 1, wherein the plurality of circumferential segments and the connecting member are configured such that radial compression of the circumferential segments exerts an axially expanding force on the connecting member.

4. The stent of claim 1, wherein each circumferential segment comprises a plurality of chevron-shaped members aligned in a same direction, and wherein each chevron-shaped member of a respective circumferential segment nests with at least one adjacent chevron-shaped member when the stent is in its axially contracted configuration.

5. The stent of claim 1, comprising a plurality of axially expandable connecting members connecting adjacent circumferential segments of the plurality of circumferential segments, wherein each connecting member is contracted axially when the stent is in its axially contracted configuration, and expanded axially when the stent is in its axially expanded configuration.

6. The stent of claim 5, wherein each circumferential segment comprises a plurality of chevron-shaped members aligned in a same direction, and wherein each chevron-shaped member of a respective circumferential segment nests with at least one adjacent chevron-shaped member when the stent is in its axially contracted configuration.

7. The stent of claim 6, wherein a chevron-shaped member of a first circumferential segment is connected via a respective one of the plurality of connecting members to a chevron-shaped member of a second circumferential segment.

8. The stent of claim 6, wherein each chevron-shaped member of a circumferential segment is connected to an adjacent chevron-shaped member of that segment by a respective connecting member.

9. The stent of claim 6, each connecting member comprising a sinusoid-shape having an amplitude that is reduced when the connecting member is expanded axially.

10. The stent of claim 6, wherein each chevron-shaped member of a respective circumferential segment is directly connected to at least one adjacent chevron-shaped member of that circumferential segment.

11. The stent of claim 6, wherein the respective circumferential segments and connecting members are configured such that, when the stent is in its axially contracted configuration, mechanical interference between adjacent circumferential segments retains the connecting members in an expanded state.

12. The stent of claim 6, wherein each connecting member is resilient and elastically expandable to change its length, such that, when the connecting member is expanded axially, it is biased to contract axially.

13. A stent configured for implantation in a body lumen, comprising:
   a plurality of radially expandable circumferential segments; and
   an axially expandable connecting member connecting adjacent circumferential segments of the plurality,
   wherein the stent has
      a relaxed configuration in which the connecting member is contracted axially, and a vertex of each circumferential segment is nested between a base and a respective vertex of at least one adjacent circumferential segment, and
      a delivery configuration in which the connecting member is expanded axially, the vertex of each circumferential segment is un-nested from the respective at least one adjacent circumferential segment, and an axial distance between adjacent circumferential segments of the plurality is greater than when the stent is in its relaxed configuration,
      wherein, when the stent is in its delivery configuration, the connecting member is biased to contract axially, and the circumferential segments are biased to expand radially, and
      wherein the plurality of circumferential segments and the connecting member are configured such that radial compression of the circumferential segments exerts an axially expanding force on the connecting member wherein, the connecting member connects a base of a first circumferential segment with a base of an adjacent circumferential segment.

14. The stent of claim 13, wherein each circumferential segment comprises a plurality of chevron-shaped members aligned in a same direction, and wherein each chevron-shaped member of a respective circumferential segment nests with at least one adjacent chevron-shaped member when the stent is in its relaxed configuration.

15. The stent of claim 13, comprising a plurality of axially expandable connecting members connecting adjacent circumferential segments of the plurality of circumferential segments, wherein each connecting member is contracted axially when the stent is in its relaxed configuration, and expanded axially when the stent is in its delivery configuration, wherein each circumferential segment comprises a plurality of chevron-shaped members aligned in a same direction, and wherein each chevron-shaped member of a respective circumferential segment nests with at least one adjacent chevron-shaped member when the stent is in its relaxed configuration.

* * * * *